United States Patent [19]

Kano et al.

[11] Patent Number: 5,601,993
[45] Date of Patent: Feb. 11, 1997

[54] ANTI-BILE ACID ANTIBODIES AND METHOD FOR ASSAYING BILE ACIDS IN FECES BY USING THE SAME

[75] Inventors: Motonari Kano, Tokyo; Masaru Matsumoto; Hiroshi Wada, both of Saitama-ken; Koki Motegi, Tokyo, all of Japan

[73] Assignees: Yuugengaisha B.S.R.; Yamato Jihan Kabushikigaisha, both of Tokyo, Japan

[21] Appl. No.: 258,483

[22] Filed: Jun. 10, 1994

[51] Int. Cl.$^6$ ........................ G01N 33/543; C07K 16/18
[52] U.S. Cl. ...................... 435/7.93; 435/7.95; 530/389.2
[58] Field of Search ................................. 435/7.93, 7.95; 530/388.9, 388.24, 389.2

[56] References Cited

U.S. PATENT DOCUMENTS

| | | | |
|---|---|---|---|
| 4,207,308 | 6/1980 | Spenney | 424/106 |
| 4,256,724 | 3/1981 | Rutner et al. | 422/68 |
| 4,264,514 | 4/1981 | Hixson, Jr. et al. | 424/1 |
| 4,273,866 | 6/1981 | Voss et al. | 435/810 |

FOREIGN PATENT DOCUMENTS

| | | |
|---|---|---|
| 1175945 | 7/1989 | Japan . |
| 324358 | 11/1992 | Japan . |

OTHER PUBLICATIONS

Kouda et al., Evaluation of Immunological Test Kit (OC–HEMODIA) for Routine Clinical Examinal of Fecal Occult Blood, Yakuri to Chiryo vol. 16, No. 3, Mar. 1988, pp. 173–181.
Gan no Rinsho, vol. 33, No. 9, Aug. (1987) pp. 48–61 with Japanese Abstract.
Igaku no Ayumi, vol. 147, No. 5 (1988) pp. 395–398 with English Abstract.
Hill, Bile Flow and Colon Cancer, Mutation Research, 238 (1990) pp. 313–320.
Medical Practice, vol. 8, No. 6 (1991) pp. 879–881, English Abstract.
Hill, The Role of Unsaturated Bile Acids in the Etiology of Large Bowel Cancer, (1977) pp. 1627–1640.
Kaibara et al., Fecal Bile Acids and Neutral Sterols . . . , Oncology, vol. 40, pp. 255–258 (1983) pp. 953–954.
Tanida et al., Fecal Bile and Analysis in Healthy Japanese . . . , Gastroenterologia Japonica, vol. 16, No. 4, (1981), pp. 363–202.
Wakayama Igaku, (1986), 37 (3) pp. 195–202, English abstract.
Igaku no Ayumi, vol. 149, No. 13, (1989), pp. 953–954, English abstract.
B. Erlanger, Methods in Enzymology, vol. 70, pp. 85–105 (1980).
R. Moorehead et al., Gut, vol. 28, pp. 1454–1459 (1987).
R. Owen et al., Nutrition and Cancer, vol. 9, pp. 67–71 (1987).
N. Rose et al., Manual of Clinical Laboratory Immunology, Third Edition, pp. 99–109, American Society for Microbiology, Washington, D.C. (1986).
Takashima et al., "Carcinogenesis in the Residual Large Bowel and Change in Metabolism of Bile Acid After Right Colectomy in Rats", Igaku no Ayumi, vol. 147, No. 5 (1988) pp. 395–398 (Full English translation).

*Primary Examiner*—Mary E. Ceperley
*Attorney, Agent, or Firm*—Cushman Darby & Cushman IP Group of Pillsbury Madison & Sutro LLP

[57] ABSTRACT

Bile acids in the feces can be easily examined on a mass scale. Further, colon cancer at an early stage can be detected and the latent colon cancer can be diagnosed. The concentration of primary bile acid (CA) in the feces is measured by an ELISA method with the use of an anti-bile acid antibody for primary bile acid which comprises anti-cholic acid-24-bovine serum-rabbit serum, the concentration of secondary bile acid (DCA) in the feces is measured by an ELISA method with the use of an anti-bile acid antibody for secondary bile acid which comprises anti-deoxycholic acid-24-bovine serum-rabbit serum, and the concentration ratio (DCA/CA) of the secondary bile acid to the primary bile acid is calculated from the measured values.

1 Claim, 1 Drawing Sheet

ANTI-BILE ACID ANTIBODIES AND METHOD FOR ASSAYING BILE ACIDS IN FECES BY USING THE SAME

FIELD OF THE INVENTION

This invention relates to anti-bile acid antibodies, which are useful in immunologically assaying primary bile acid and secondary bile acid in feces respectively, and a method for assaying bile acids in feces by using these antibodies.

BACKGROUND OF THE INVENTION

It is well known that the number of colon cancer cases has recently been remarkably increasing in Japan. This rise is partly attributable to the adoption of Western-style dietary habits.

It is highly important to discover colon cancer at an early stage from the viewpoints of both prevention and treatment. Known methods for the early detection of colon cancer include use of tumor markers in blood, detection of human blood in feces and image diagnosis. Among these methods, detection of human blood in feces may be cited as an inexpensive test method which can be carried out with little burden on a patient [*Yakuri to Chiryo*, Vol. 16, No. 3, March (1988) pp. 173–181; and *Gan no Rinsho*, Vol. 33, No. 9, August (1987) pp. 48–61]. However, this method, which comprises detecting hemoglobin due to hemorrhage from a cancer tissue by using a monoclonal antibody, cannot be regarded as an excellent method, since it suffers from some problems in, for example, distinguishing hemorrhage caused by some factor other than cancer and a change in hemoglobin with the lapse of time.

Regarding a casual relationship between bile acids and the incidence of colon cancer, it has been pointed out that bile acids, in particular, secondary bile acids act as a promoter in the pathogenesis colon cancer (i.e., a so-called auxiliary substance in oncogenesis) by immunological studies and animal experiments both in Japan and abroad [*Igaku no Ayumi*, Vol. 147, No. 5 (1988) pp. 395–398; *Mutation Research*, 238 (1990) pp. 313–320; *Medical Practice*, Vol. 8, No. 6 (1991) pp. 879–881; and Hill. M. J.: *The role of unsaturated bile acids in the etiology of large bowel cancer*, in *Origins of Human Cancer.*, ed. by Watson. J. D. and Winstein. J. A., *Cold Spring Habor Conference on cell proliferation*, Vol. 4. Cold Spring Habor Laboratory, New York pp. 1627–1640, (1977); and Oncology 40: pp. 255–258 (1983)]. In a pilot test performed by the present inventors, a large amount of secondary bile acids were detected in colon cancer patients.

On the other hand, bile acids produced in the liver are discharged into the gallbladder in the form of the primary bile acids (cholic acid: CA) and concentrated therein. Next, they are released to the bowels by meal stimulation. Then they emulsify fats and lipids and thus facilitate the absorption of these substances from the intestinal wall. Most bile acids per se repeat the closed enterohepatic circulation where they are reabsorbed mainly in the ileum and returned to the liver through the portal vein. However, some bile acids are discharged in the feces and are reduced into their secondary bile acids (deoxycholic acid: DCA) by enterobacteria. Accordingly, fecal bile acids are mostly free-type secondary bile acids [Tanida N, Hisaka Y, Hosomi M. et al.: Fecal bile acid analysis in healthy japanese subjects using a lipophilic anion exchanger, capillary column gas chromatography and mass spectrometry. *Gastroenterologia jpn* 16: 363, 1981; and *Wakayama Igaku*, (1986), 37 (3) pp. 195–202].

In clinical practice, it is known that the amount and composition of fecal bile acids are changed in various diseases in digestive tracts or after the excision of digestive tracts [*Igaku no Ayumi*, Vol. 149. No. 13 (1989) pp. 953–954; *Medical Practice*, Vol. 8, No. 6 (1991) pp. 879–881].

Analysis of fecal bile acids is important in the clarification of the metabolic mechanism of bile acids. Conventional methods for analyzing these bile acids include GLC (gas-liquid chromatography) and GC-MS (gas-liquid chromatography-mass spectrometry). Further, there have been known a simplified method for measuring bile acids in human feces with the use of hydroxysteroid dehydrogenase ($3\alpha$-HSD, $7\alpha$-HSD) for mass assay and an enzyme fluorescent method as its improved method.

However, the above-mentioned GLC and GC-MS require complicated analytical procedures and a high degree of knowledge and technique, which makes them less applicable to mass assay.

On the other hand, the latter enzyme fluorescent method is disadvantageous since it still suffers from the problem of $\beta$-hydroxybile acid in feces and requires the preparation of freeze-dried feces after the collection and extraction and purification of bile acids. Thus this method is less applicable to mass assay too. Moreover, these tests are designed to measure only the total bile acids. Namely, neither the respective contents of the primary and secondary bile acids nor the composition can be clarified thereby. Thus the enzyme fluorescent method is less useful in screening colon cancer.

The present invention has been completed in order to solve the above-mentioned problems. Thus it aims at providing anti-bile acid antibodies, which can be effectively used as an immunological assay reagent for measuring and examining primary and secondary bile acids in feces to thereby make it possible to detect colon cancer at an early stage and to identify latent colon cancer, and a method for assaying bile acids in feces by using these antibodies.

SUMMARY OF THE INVENTION

In order to achieve the above-mentioned object, the anti-bile acid antibody for primary bile acid of the present invention comprises anti-cholic acid-24-bovine serum albumin-rabbit serum.

The anti-bile acid antibody for secondary bile acid of the present invention comprises anti-deoxycholic acid-24-bovine serum albumin-rabbit serum.

The method for assaying bile acids in feces according to the present invention is characterized by comprising measuring the concentration of primary bile acid in feces by an ELISA method with the use of the anti-bile acid antibody for the primary bile acid, measuring the concentration of secondary bile acid by an ELISA method with the use of the anti-bile acid antibody for the secondary bile acid and then calculating the concentration ratio (DCA/CA) of the secondary bile acid (DCA) to the primary bile acid (CA) from the measured values.

DETAILED DESCRIPTION OF THE INVENTION

Figure 1:
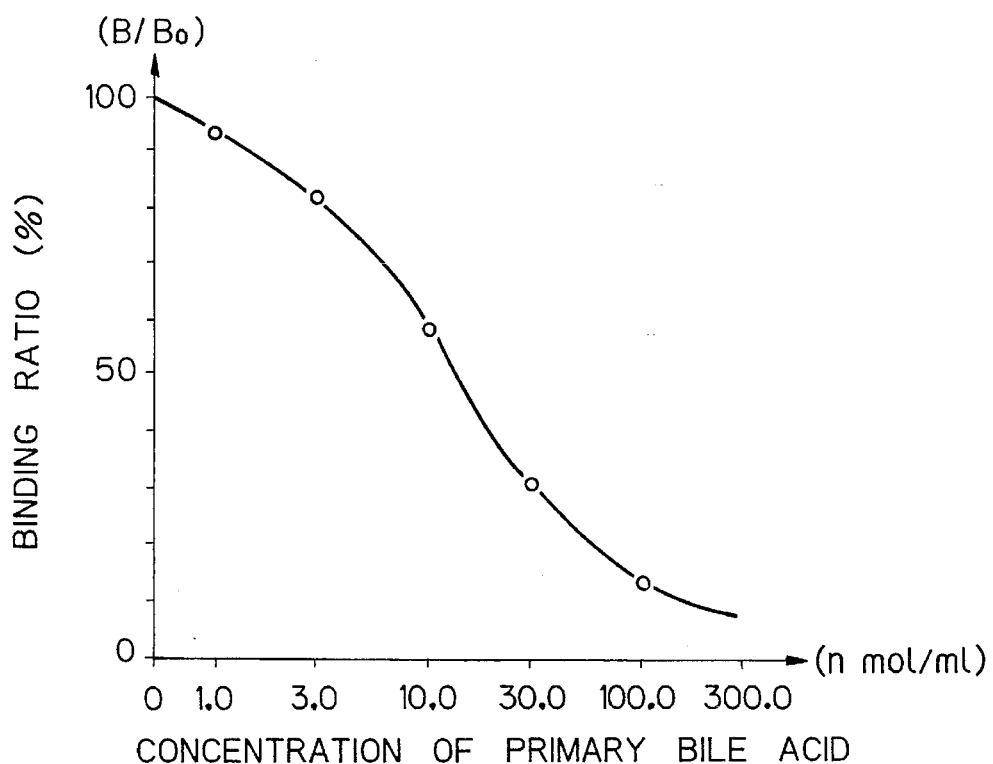
FIG. 1 shows a standard curve of primary bile acid in the example.

In the present invention, primary bile acid in feces can be easily measured by an enzyme-linked immunosorbent assay (ELISA) method with the use of an anti-bile acid antibody which is prepared from rabbit serum having bovine serum albumin at the 24-position of a cyclic compound of anti-cholic acid and reacts specifically with the primary bile acid in feces.

Further, secondary bile acid in feces can be easily measured by an enzyme-linked immunosorbent assay (ELISA) method with the use of an anti-bile acid antibody which is prepared from rabbit serum having bovine serum albumin at the 24-position of a cyclic compound of anti-deoxycholic acid and reacts specifically with the secondary bile acid in feces.

Furthermore, the calculation of the concentration ratio of the secondary bile acid to the primary bile acid makes it possible to accurately determine the content of the secondary bile acid, acting as a promoter in the pathogenesis of colon cancer, in feces and largely contributes to the detection of colon cancer at an early stage and the diagnosis of latent colon cancer.

EXAMPLE

Methods for preparing the anti-cholic acid-24-bovine serum albumin-rabbit serum of the present invention which reacts specifically with primary bile acid in human feces and the anti-deoxycholic acid-24-bovine serum albumin-rabbit serum of the present invention which reacts specifically with secondary bile acid in human feces is illustrated hereafter.

(Anti-cholic acid-24-bovine serum albumin-rabbit serum)

(a) 41 mg of cholic acid was dissolved in 1 ml of dioxane. To this solution, 23 mg of N-hydroxysuccinimide and 38 mg of 1-ethyl-3-carbodiimide hydrochloride were added. The mixture thus obtained was reacted at room temperature for 3 hours.

(b) To this reaction mixture, 4 ml of ethyl acetate and 4 ml of distilled water were added. After the completion of the extraction, the aqueous layer was removed and 4 ml of distilled water was newly added to effect the extraction again. After removing the aqueous layer, the ethyl acetate layer was dehydrated over anhydrous sodium acetate and evaporated to dryness to thereby give cholic acid active ester.

(c) Next, 30 mg of the cholic acid active ester obtained above was dissolved in 1 ml of dimethylformamide. The resulting solution was then slowly added to an aqueous solution of bovine serum albumin (BSA), which had been prepared by dissolving 100 mg of BSA in 4 ml of distilled water, while maintaining the pH value to 7 to 8 by addition of 1 N NaOH.

(d) About 30 minutes thereafter, the solution was dialyzed against distilled water over day and night to thereby give an antigen.

(e) A rabbit was immunized with 1 mg per dose of the antigen thus obtained for 4 months. Then an anti-cholic acid antibody acting as an antibody specific to cholic acid, which had been thus formed in the body of the rabbit, was harvested to thereby give anti-cholic acid-24-bovine serum albumin-rabbit serum (hereinafter referred to simply as anti-cholic acid antiserum).

This anti-cholic acid antiserum is used in the assay of primary bile acid in human feces by the ELISA (enzyme linked immunosorbent assay) method.

(Anti-deoxycholic acid-24-bovine serum albumin-rabbit serum)

(a) 40 mg of deoxycholic acid was dissolved in 1 ml of dioxane. To this solution, 23 mg of N-hydroxysuccinimide and 38 mg of 3-dimethylaminopropyl carbodiimide hydrochloride were added. The mixture thus obtained was reacted at room temperature for 3 hours.

(b) To this reaction mixture, 4 ml of ethyl acetate was added. After the completion of the extraction, the aqueous layer was removed and 4 ml of distilled water was newly added to effect the extraction again. After removing the aqueous layer, the ethyl acetate layer was dehydrated over anhydrous sodium acetate and evaporated to dryness to thereby give deoxycholic acid active ester.

(c) Next, 30 mg of the deoxycholic acid active ester obtained above was dissolved in 1 ml of dimethylformamide. The resulting solution was then slowly added to an aqueous solution of bovine serum albumin (BSA), which had been prepared by dissolving 100 mg of BSA in 4 ml of distilled water, while maintaining the pH value to 7 to 8 with the use of 1 N NaOH.

(d) About 30 minutes thereafter, the solution was dialyzed against distilled water over day and night to thereby given an antigen.

(e) A rabbit was immunized with 1 mg per dose of the antigen thus obtained for 4 months. Then an anti-deoxycholic acid antibody acting as an antibody specific to deoxycholic acid, which had been thus formed in the body of the rabbit, was harvested to thereby give anti-deoxycholic acid-24-bovine serum albumin-rabbit serum (hereinafter referred to simply as anti-deoxycholic acid antiserum).

This anti-deoxycholic acid antiserum is used in the assay of secondary bile acid in human feces by the ELISA method.

The method for assaying the primary and secondary bile acids in feces by ELISA with the use of the anti-cholic acid antiserum and anti-deoxycholic acid antiserum thus prepared is explained hereafter.

(Assay of primary bile acid)

First, 500 µl of a buffer solution was added to one drop of a fecal solution in a Hemodia feces sampler to thereby prepare a diluted fecal solution to be assayed.

The buffer solution was prepared from a 0.05M phosphate buffer (pH 7.2), 0.30M of NaCl, 1 mM of ethylenediaminetetraacetic acid (EDTA), 0.1% of BSA and 0.1% of $NaN_3$.

Next, a secondary antibody coated-plate was immersed in a mixture comprising 50 µl of the above-mentioned diluted fecal solution, 50 µl of an anti-cholic acid antiserum solution prepared by diluting the anti-cholic acid antiserum 15000-fold and 50 µl of an enzyme-labeled cholic acid (i.e., enzyme-labeled antigen) solution and reacted at 25° C. for 3 hours. After the completion of the reaction, the secondary antibody-coated plate was washed with a washing liquor thrice.

Then a substrate (color development) solution comprising σ-nitrophenyl-β-D-galactopyranoside was added to the plate in 150 µl portions and reacted at 25° C. for 90 minutes. Subsequently, a stopping reagent comprising 0.2M $Na_2CO_3$ was added in 100 µl portions to thereby cease the reaction.

Then the absorbance of the plate was measured at a definite wavelength (405 nm) by using a microplate spectrophotometer. Based on the absorbance thus measured, a standard curve was calibrated and then the concentration of primary bile acid in the feces was determined therefrom.

Table 1 shows the results of the measurement of the absorbance at standard concentrations of primary bile acid ranging from 0 to 300 n mol/ml.

TABLE 1

| | Standard conc. (n mol/ml) | Absorbance (at 405 nm) | $B/B_o$ | Theoretical conc. | Average |
|---|---|---|---|---|---|
| 1 | 0.0 | 2.196 | 100.94 | lower | *** |
|   |     | 2.155 | 99.06  | lower |     |
| 2 | 1.0 | 1.997 | 91.79  | 1.23  | 1.02 |
|   |     | 2.051 | 94.28  | 0.80  |      |
| 3 | 3.0 | 1.815 | 83.43  | 2.82  | 3.07 |
|   |     | 1.769 | 81.31  | 3.32  |      |
| 4 | 10.0| 1.325 | 60.91  | 9.12  | 9.97 |
|   |     | 1.241 | 57.04  | 10.82 |      |
| 5 | 30.0| 0.685 | 31.49  | 32.36 | 31.08|
|   |     | 0.710 | 32.64  | 29.80 |      |
| 6 |100.0| 0.310 | 14.25  | 104.77| 99.77|
|   |     | 0.329 | 15.12  | 94.77 |      |
| 7 |300.0| 0.160 | 7.35   | 304.27| 302.19|
|   |     | 0.161 | 7.40   | 300.10|      |

FIG. 1 is a standard curve which shows the binding ratio ($B/B_O$) of the primary bile acid (CA) to the anti-cholic acid antiserum of the present invention.

The standard curve given in FIG. 1 shows typical characteristics of the ELISA method, which indicates that primary bile acid in feces can be directly and conveniently measured by this enzyme immunoassay method without employing any complicated treatments or measuring procedures required in the conventional methods. Thus mass assay can be conducted at a low cost.

(Assay of secondary bile acid)

A secondary antibody coated-plate was immersed in a mixture comprising 50 μl of the diluted fecal solution which had been prepared in the same manner as the one employed in the assay of primary bile acid, 50 μl of an anti-deoxycholic acid antiserum solution prepared by diluting the anti-deoxycholic acid antiserum 15000-fold and 50 μl of an enzyme-labeled deoxycholic acid (i.e., enzyme-labeled antigen) solution and reacted at 25° C. for 3 hours. After the completion of the reaction, the secondary antibody-coated plate was washed with a washing liquor thrice.

Then a substrate (color development) solution comprising o-nitrophenyl-β-D-galactopyranoside was added to the plate in 150 μl portions and reacted at 25° C. for 90 minutes. Subsequently, a stopping reagent comprising 0.2M $Na_2CO_3$ was added in 100 μl portions to thereby cease the reaction.

Then the absorbance of the plate was measured at a definite wavelength (405 nm) by using a microplate spectrophotometer. Based on the absorbance of the plate thus measured, a standard curve was formed and then the concentration of the secondary bile acid in the feces was determined therefrom.

Table 2 shows the results of the measurement of the absorbance at standard concentrations of secondary bile acid ranging from 0 to 300 n mol/ml.

TABLE 2

| | Standard conc. (n mol/ml) | Absorbance (at 405 nm) | $B/B_o$ | Theoretical conc. | Average |
|---|---|---|---|---|---|
| 1 | 0.0 | 2.053 | 101.34 | lower | *** |
|   |     | 1.979 | 98.16  | lower |     |
| 2 | 3.0 | 1.844 | 91.47  | lower | *** |
|   |     | 1.867 | 92.61  | lower |     |
| 3 | 10.0| 1.607 | 79.71  | 11.30 | 10.65 |
|   |     | 1.637 | 81.20  | 10.00 |       |
| 4 | 30.0| 1.271 | 63.05  | 29.11 | 30.33 |
|   |     | 1.244 | 61.71  | 31.54 |       |
| 5 |100.0| 0.805 | 39.93  | 85.15 | 91.99 |
|   |     | 0.743 | 36.86  | 98.84 |       |
| 6 |300.0| 0.356 | 17.66  | 335.01| 340.13|
|   |     | 0.349 | 17.31  | 345.25|       |

Figure 2:
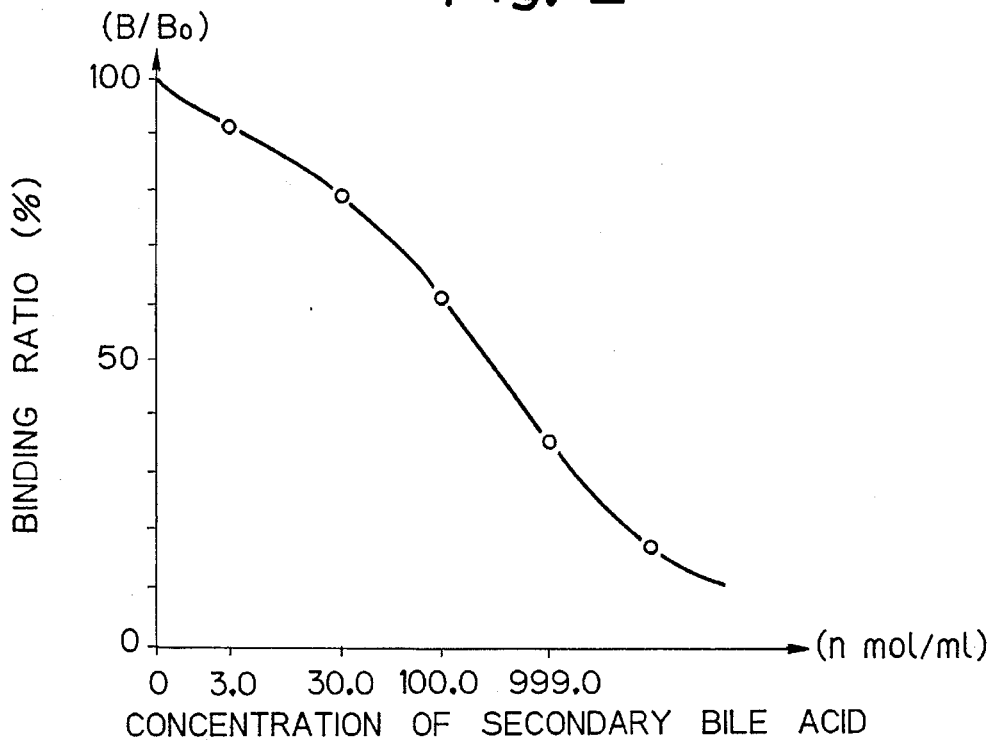
FIG. 2 shows a standard curve of secondary bile acid in the example.

FIG. 2 is a standard curve which shows the binding ratio ($B/B_O$) of the secondary bile acid (DCA) to the anti-deoxycholic acid antiserum of the present invention.

The standard curve given in FIG. 2 shows typical characteristics of the ELISA method, which indicates that the secondary bile acid in feces can be directly and conveniently measured by this enzyme immunoassay method without employing any complicated treatments or measuring procedures required in the conventional methods. Thus mass assay can be conducted at a low cost.

Table 3 indicates the cross-reaction rates (specificities) of primary and secondary bile acids with the corresponding anti-cholic acid antibody and anti-deoxycholic acid antibody against these bile acids.

TABLE 3

| Bile acid | Anti-CA antibody (%) | Anti-DCA antibody (%) |
|---|---|---|
| Cholic acid | 100 | 1.5 |
| Glycocholic acid | 192 | 3.4 |
| Taurocholic acid | 202 | 4.9 |
| Deoxycholic acid | 4.6 | 100 |
| Glycodeoxycholic acid | 7.1 | 184 |
| Taurodeoxycholic acid | 8.4 | 192 |

As Table 3 clearly shows, cholic acid, glycocholic acid and taurocholic acid, which are primary bile acids, specifically react with the corresponding anti-cholic acid antibody, while deoxycholic acid, glycodeoxycholic acid and taurodeoxycholic acid, which are secondary bile acids, specifically react with the corresponding anti-deoxycholic acid antibody.

Next, composition ratios (DCA/CA) of secondary bile acid (DCA) to primary bile acid (CA) were discussed with reference to Table 4.

TABLE 4

| Sex | Age | Case | Dukes (grade/stage) | DCA | CA | DCA/CA | |
|---|---|---|---|---|---|---|---|
| M | 62 | Transverse colon | A/I | 394.0 | 162.0 | 2.432 | Preoperative |
|   |    |                  |     | 543.8 | 170.2 | 3.841 | Preoperative |

TABLE 4-continued

| Sex | Age | Case | Dukes (grade/stage) | DCA | CA | DCA/CA | |
|---|---|---|---|---|---|---|---|
| | | | | 341.2 | 754.4 | 0.452 | Post-operative (9 days) |
| | | | | 178.7 | 314.4 | 0.568 | Post-operative (10 days) |
| F | 54 | Sigmoid colon | A/I | 365.7 | 149.0 | 2.45 | Pre-operative |
| | | | | 70.4 | 844.6 | 0.083 | Post-operative (7 days) |
| F | 57 | Rectum | B/II | 326.6 | 113.3 | 2.88 | Pre-operative |
| | | | | 243.2 | 85.3 | 2.85 | Post-operative (13 days) |
| M | 58 | Sigmoid Colon | C/III | 768.4 | 213.1 | 3.60 | Pre-operative |
| | | | | 173.8 | 136.3 | 1.27 | Post-operative (13 days) |
| M | 62 | Ascending colon | B/III | 85.9 | 99.5 | 0.864 | Pre-operative |
| | | | | 211.6 | 1021.5 | 0.207 | Post-operative (7 days) |
| | | | | 99.7 | 1310.1 | 0.076 | Post-operative (24 days) |
| M | 54 | Rectum | C/V | 59.6 | 53.0 | 1.12 | Pre-operative |
| | | | | 70.4 | 1916.2 | 0.036 | Post-operative (6 days) |
| M | 56 | Rectum | C/V | 555.0 | 152.9 | 3.629 | Pre-operative |
| | | | | 46.1 | 42.3 | 1.090 | Post-operative (2 days) |

Table 4 shows compositions and ratios of bile acids in feces of clinical cases of colon cancers in accordance with Dukes' classification which has been internationally employed.

As Table 4 clearly shows, in the post-operative dynamics of bile acid metabolism, the concentration of secondary bile acid (DCA) in feces of 6 colon cancer patients (among 7 cases) tended to remarkably increase, compared to primary bile acid (CA). DCA was remarkably decreased in 5 post-operative cases, while CA was remarkably increased in 4 post-operative cases.

Although slightly different dynamics of DCA and CA were observed in some cases, the DCA/CA ratio tended to decrease after the operation in every case. It is therefore considered that the evaluation based on the DCA/CA ratio can be advantageously applied to clinical purposes.

As discussed above, it has been proved that the screening method, which comprises measuring the primary and secondary bile acids in the pre-operative and post-operative feces of a colon cancer patient and analyzing the ratio of these bile acids, is clinically useful. Further, it is expected that a colon cancer lesion at an early stage can be detected or a latent colon cancer can be diagnosed by this method.

What is claimed is:

1. A method of detecting colon cancer and latent colon cancer comprising the steps of:

measuring the concentration of primary bile acid in feces by an ELISA method employing an anti-bile acid antibody for the primary bile acid, said antibody prepared in a rabbit in response to cholic acid-24-BSA used as the immunogen;

measuring the concentration of secondary bile acid in the feces by an ELISA method employing an anti-bile acid antibody for the secondary bile acid, said antibody prepared in a rabbit in response to deoxycholic acid-24-BSA used as the immunogen;

calculating the concentration ratio of the secondary bile acid to the primary bile acid from the measured concentrations; and employing the concentration ratio as a diagnostic indicator of said colon cancer.

* * * * *